(12) United States Patent
Sereno et al.

(10) Patent No.: US 10,098,985 B2
(45) Date of Patent: Oct. 16, 2018

(54) DENTAL IMPLANT INCORPORATING AN APATITE

(71) Applicant: JUVORA LIMITED, Lancashire (GB)

(72) Inventors: Nuno Sereno, Southport Merseyside (GB); Marcus Jarman-Smith, Lytham St. Annes Merseyside (GB); Reinhard Lobenhofer, Nuremberg (DE)

(73) Assignee: JUVORA LIMITED, Lancashire (GB)

( * ) Notice: Subject to any disclaimer, the term of this patent is extended or adjusted under 35 U.S.C. 154(b) by 133 days.

(21) Appl. No.: 15/106,166

(22) PCT Filed: Dec. 17, 2014

(86) PCT No.: PCT/GB2014/053736
§ 371 (c)(1),
(2) Date: Jun. 17, 2016

(87) PCT Pub. No.: WO2015/092398
PCT Pub. Date: Jun. 25, 2015

(65) Prior Publication Data
US 2016/0317712 A1 Nov. 3, 2016

(30) Foreign Application Priority Data

Dec. 19, 2013 (GB) .................................. 1322506.5
Dec. 19, 2013 (GB) .................................. 1322564.4

(51) Int. Cl.
*A61L 27/46* (2006.01)
*A61C 13/00* (2006.01)
*A61C 8/00* (2006.01)
*A61C 5/70* (2017.01)

(52) U.S. Cl.
CPC ................ *A61L 27/46* (2013.01); *A61C 5/70* (2017.02); *A61C 8/0013* (2013.01); *A61C 8/0016* (2013.01); *A61C 8/0022* (2013.01); *A61C 8/0051* (2013.01); *A61C 8/0069* (2013.01); *A61C 8/0074* (2013.01); *A61C 8/0075* (2013.01); *A61C 8/0089* (2013.01); *A61C 8/0095* (2013.01); *A61C 13/0004* (2013.01); *A61L 2430/12* (2013.01)

(58) Field of Classification Search
CPC ......... A61L 27/46; A61C 5/70; A61C 8/0013; A61C 8/0016; A61C 8/0022; A61C 8/0051; A61C 8/0069; A61C 8/0074; A61C 8/0075; A61C 8/0089; A61C 8/0095; A61C 13/0004
See application file for complete search history.

(56) References Cited

U.S. PATENT DOCUMENTS

| 5,872,159 A | 2/1999 | Cougoulic |
| 2004/0241614 A1 | 12/2004 | Goldberg et al. |
| 2007/0015110 A1 | 1/2007 | Zhang et al. |
| 2008/0050699 A1 | 2/2008 | Zhang et al. |
| 2009/0098511 A1 | 4/2009 | Zhang |
| 2010/0145393 A1 | 6/2010 | Fallin et al. |
| 2013/0178900 A1 | 7/2013 | Fallin et al. |
| 2014/0035201 A1 | 2/2014 | Jarman-Smith et al. |

FOREIGN PATENT DOCUMENTS

| GB | 2 496 981 A | 5/2013 |
| WO | WO 2006/127838 A2 | 11/2006 |
| WO | WO 2012/110803 A1 | 8/2012 |
| WO | WO 2013/070493 A1 | 5/2013 |

OTHER PUBLICATIONS

International Search Report (PCT/ISA/210) dated Mar. 17, 2015, by the European Patent Office as the International Searching Authority for International Application No. PCT/GB2014/053736.
Written Opinion (PCT/ISA/237) dated Mar. 17, 2015, by the European Patent Office as the International Searching Authority for International Application No. PCT/GB2014/053736.
United Kingdom Search Report dated Jun. 9, 2015 for Application No. GB1422507.2.
D. J. Blundell et al., "The Morphology of Poly(Aryl-Ether-Ether-Ketone", Polymer, Aug. 1983, vol. 24, pp. 953-958.
Marc Bohner et al., "Can Bioactivity Be Tested In Vitro With BSF Solution?", Biomaterials, vol. 30, 2009, pp. 2175-2179.
Tadashi Kokubo et al., "How Useful is BSF in Predicting In Vivo Bone Bioactivity?", Biomaterials, vol. 27, 2006, pp. 2907-2915.
U.S. Appl. No. 15/106,051, filed Jun. 17, 2016, Nuno Sereno.
U.S. Appl. No. 15/106,100, filed Jun. 17, 2016, Nuno Sereno.

*Primary Examiner* — Edward J Cain
(74) *Attorney, Agent, or Firm* — Buchanan Ingersoll & Rooney PC

(57) ABSTRACT

A dental implant comprises a composition which comprises a polymeric material which is preferably polyetheretherketone, and an apatite, for example a hydroxy-containing apatite. A prosthodontics device may comprise a dental implant made from polyetheretherketone, an abutment, also made from PEEK, and a crown, which is also made from PEEK by machining from a PEEK disc.

13 Claims, 4 Drawing Sheets

DENTAL IMPLANT INCORPORATING AN APATITE

This invention relates to a prosthodontics device and particularly, although not exclusively, relates to a dental implant incorporating an apatite.

Prosthodontics devices are arranged to address missing or deficient teeth in patients. One type of prosthodontics device may be fixed within a patient's mouth, for example by screws or adhesive, and is not intended to be removed under normal conditions. Such a device may comprise an implant which is osseointegrated into a patient's jaw bone. A framework incorporating a crown or bridge may then be substantially permanently secured to the implant via an abutment.

The implant of the device is a root device which is usually made from pure titanium since titanium readily osseointegrates into the jaw bone and has sufficient strength to withstand the loads to which it is subjected in use. In some cases, surfaces of the titanium may be modified by plasma spraying, sandblasting, anodizing or etching to increase the surface area and enhance osseointegration potential of the implant.

The crown or bridge of the device may include a metal, for example, titanium framework, onto which prosthetic teeth and gums are formed. The abutment which may also be made from metal is arranged to join the osseointegrated implant to the crown or bridge.

Prosthodontic devices as described are in widespread use. However, the devices tend to be relatively stiff and inflexible. There is therefore a risk of stress shielding whereby the implant may work loose over time, particularly if the quality or quantity of the bone available around the implant site is poor. Furthermore, since implants lack a periodontal ligament (which in natural teeth attaches teeth to the bone) prosthetic devices as described feel slightly different from natural teeth during chewing.

There have been proposals to make implants of prosthetic devices from polymeric materials. However, it is challenging to select suitable polymeric materials which are able to be osseointegrated into bone and have mechanical properties which are sufficient to withstand the high loads to which implants are subjected in use. It is a first object of the invention to address the aforementioned problems. Preferred embodiments have an object of providing an implant which can be satisfactorily osseointegrated and which has acceptable mechanical properties.

Furthermore, prosthetic devices as described tend to be relatively expensive and/or comprise components which are often individually made by different people/organisations and often from different materials. For example, multinational companies supply precision machined titanium screws at relatively high cost. They may also supply abutments. Local Dental Technicians may make the framework including crowns and/or bridges which may be secured to the abutments.

It is a second object of preferred embodiments of the present invention to provide a prosthodontics device with improved flexibility and/or mouth feel. Especially preferred embodiments of the invention aim to provide a prosthodontics device which can be provided at relatively low cost and/or which is relatively easy to manufacture.

According to a first aspect of the invention, there is produced a dental implant arranged to be secured within the jaw bone of a patient, wherein said implant comprises a composition which comprises a polymeric material and an apatite, for example an hydroxyl-containing apatite (especially hydroxyapatite), wherein said polymeric material comprises a repeat unit of formula (I)

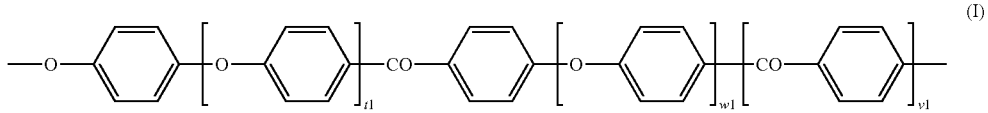

where t1 and w1 independently represent 0 or 1 and v1 represents 0, 1 or 2, wherein the ratio of the wt % of said polymeric material divided by the wt % of said apatite (e.g. hydroxyapatite) is in the range 1 to 9.

Unpredictably, it has been found that a dental implant as described has both excellent mechanical properties (which enable implants having thin walls and/or small dimensions to be manufactured) and excellent osseointegration properties.

Said polymeric material preferably consists essentially of a repeat unit of formula I. Preferred polymeric materials comprise (especially consist essentially of) a said repeat unit wherein t1=1, v1=0 and w1=0; t1=0, v1=0 and w1=0; t1=0, w1=1, v1=2; or t1=0, v1=1 and w1=0. More preferred comprise (especially consist essentially of) a said repeat unit wherein t1=1, v1=0 and w1=0; or t1=0, v1=0 and w1=0. The most preferred comprises (especially consists essentially of) a said repeat unit wherein t1=1, v1=0 and w1=0.

In preferred embodiments, said polymeric material is selected from polyetheretherketone, polyetherketone, polyetherketoneetherketoneketone and polyetherketoneketone. In a more preferred embodiment, said polymeric material is selected from polyetherketone and polyetheretherketone. In an especially preferred embodiment, said polymeric material is polyetheretherketone.

Said polymeric material may have a Notched Izod Impact Strength (specimen 80 mm×10 mm×4 mm with a cut 0.25 mm notch (Type A), tested at 23° C., in accordance with ISO180) of at least 4 KJm$^{-2}$, preferably at least 5 KJm$^{-2}$, more preferably at least 6 KJm$^{-2}$. Said Notched Izod Impact Strength, measured as aforesaid, may be less than 10 KJm$^{-2}$, suitably less than 8 KJm$^{-2}$.

Said polymeric material may have a tensile strength, measured in accordance with ISO527 (specimen type 1b) tested at 23° C. at a rate of 50 mm/minute of at least 20 MPa, preferably at least 60 MPa, more preferably at least 80 MPa. The tensile strength is preferably in the range 80-110 MPa, more preferably in the range 80-100 MPa.

Said polymeric material may have a flexural strength, measured in accordance with ISO178 (80 mm×10 mm×4 mm specimen, tested in three-point-bend at 23° C. at a rate of 2 mm/minute) of at least 50 MPa, preferably at least 100 MPa, more preferably at least 145 MPa. The flexural strength is preferably in the range 145-180 MPa, more preferably in the range 145-164 MPa.

Said polymeric material may have a flexural modulus, measured in accordance with ISO178 (80 mm×10 mm×4 mm specimen, tested in three-point-bend at 23° C. at a rate of 2 mm/minute) of at least 1 GPa, suitably at least 2 GPa, preferably at least 3 GPa, more preferably at least 3.5 GPa. The flexural modulus is preferably in the range 3.5-4.5 GPa, more preferably in the range 3.5-4.1 GPa.

Said composition may have a Notched Izod Impact Strength (specimen 80 mm×10 mm×4 mm with a cut 0.25 mm notch (Type A), tested at 23° C., in accordance with ISO180) of at least 3.5 KJm$^{-2}$, preferably at least 4.5 KJm$^{-2}$, more preferably at least 5.5 KJm$^{-2}$. Said Notched Izod Impact Strength, measured as aforesaid, may be less than 10 KJm$^{-2}$, suitably less than 8 KJm$^{-2}$.

Said composition may have a tensile strength, measured in accordance with ISO527 (specimen type 1 b) tested at 23° C. at a rate of 50 mm/minute of at least 20 MPa, preferably at least 60 MPa, more preferably at least 80 MPa. The tensile strength is preferably in the range 80-120 MPa, more preferably in the range 80-110 MPa.

Said composition may have a flexural strength, measured in accordance with ISO178 (80 mm×10 mm×4 mm specimen, tested in three-point-bend at 23° C. at a rate of 2 mm/minute) of at least 50 MPa, preferably at least 100 MPa, more preferably at least 145 MPa. The flexural strength is preferably in the range 145-190 MPa, more preferably in the range 145-175 MPa.

Said composition may have a flexural modulus, measured in accordance with ISO178 (80 mm×10 mm×4 mm specimen, tested in three-point-bend at 23° C. at a rate of 2 mm/minute) of at least 1 GPa, suitably at least 2 GPa, preferably at least 3 GPa, more preferably at least 3.5 GPa. The flexural modulus is preferably in the range 3.5-6.0 GPa, more preferably in the range 4.5-5.5 GPa.

Said polymeric material suitably has a melt viscosity (MV) of at least 0.06 kNsm$^2$, preferably has a MV of at least 0.09 kNsm$^{-2}$, more preferably at least 0.12 kNsm$^{-2}$, especially at least 0.15 kNsm$^{-2}$. Advantageously, the MV may be at least 0.35 kNsm$^{-2}$ and especially at least 0.40 kNsm$^{-2}$. Said polymeric material may have a MV of less than 1.00 kNsm$^{-2}$, preferably less than 0.5 kNsm$^{-2}$. An MV in the range 0.4 to 0.5 kNsm$^{-2}$ has been found to be particularly advantageous in the manufacture of accurate, strong frameworks.

MV is suitably measured using capillary rheometry operating at 400° C. at a shear rate of 1000 s$^{-1}$ using a tungsten carbide die, 0.5 mm×3.175 mm.

Said polymeric material may be amorphous or semi-crystalline. It is preferably crystallisable. It is preferably semi-crystalline.

The level and extent of crystallinity in a polymer is preferably measured by wide angle X-ray diffraction (also referred to as Wide Angle X-ray Scattering or WAXS), for example as described by Blundell and Osborn (Polymer 24, 953, 1983). Alternatively, crystallinity may be assessed by Differential Scanning Calorimetry (DSC).

The level of crystallinity of said polymeric material (suitably measured by DSC) may be at least 1%, suitably at least 3%, preferably at least 5% and more preferably at least 10%. In especially preferred embodiments, the crystallinity may be greater than 25%. It may be less than 50% or less than 40%. Preferably the prosthodontics device includes a framework having the aforementioned levels of crystallinity.

The main peak of the melting endotherm (Tm) of said polymeric material (if crystalline) may be at least 300° C.

Said composition may include said polymeric material, said apatite and other components, for example colourants (e.g. pigments, ceramics, metal oxides (eg. titanium dioxide)). Said composition may include 0-10 wt %, suitably 0-6 wt % of colourants. Colourants may be selected so the composition is pink or white. Colourants may occur so that the colour is graduated. In one embodiment, the composition includes less than 1 wt %, for example no colourant.

Said composition preferably includes 1 wt % or less, preferably 0 wt % of fibrous fillers.

Said composition preferably includes 1 wt % or less, preferably 0 wt % of carbon fibre.

The ratio of the wt % of said polymeric material divided by the wt % of said apatite may be in the range 2.3 to 9, is suitably in the range 2.7 to 5.6, preferably in the range 3 to 5, more preferably in the range 3.5 to 4.5, especially in the range 3.8 to 4.2 or 3.9 to 4.1.

Said composition suitably includes at least 65 wt %, preferably at least 70 wt %, more preferably at least 75 wt % of said polymeric material, and may include at least 10 wt %, preferably at least 15 wt %, more preferably at least 18 wt % of said apatite. The balance in said composition may be made up of other fillers, for example colourants. Preferably, the sum of the wt % of said polymeric material and said apatite is in the range 90 to 100 wt %, more preferably in the range 95 to 100 wt %, especially 99 to 100 wt %.

Said apatite may optionally comprise a material that has been modified or doped with one or more additional chemical elements. For example, it may comprise a material that has been modified or doped with one or more metals. The apatite may for example comprise hydroxyapatite that has optionally been modified or doped. The hydroxyapatite may for example optionally be modified or doped with one or more metals. The hydroxyapatite may for example be optionally modified or doped with boron, magnesium, silicate or silver.

The apatite may comprise a material optionally doped with one or more of silicate ($SiO_4^{2-}$), Borate ($BO_3^{3-}$) and Strontium ($Sr^{2+}$). Suitably, the total content of silicate ($SiO_4^{2-}$), Borate ($BO_3^{3-}$) and Strontium ($Sr^{2+}$) within the apatite does not exceed 10% by molarity as a cumulative value.

Said apatite may comprise one or more of Silicon (Si), Fluorine (F), Sulphur (S), Boron (B), Strontium (Sr), Magnesium (Mg), Silver (Ag), Barium (Ba), Zinc (Zn), Sodium (Na), Potassium (K), Aluminium (Al), Titanium (Ti) and Copper (Cu).

Said apatite may comprise a material comprising a calcium phosphate lattice, for example a hydroxyapatite lattice in which, optionally, single or multiple elements have been introduced. For example the apatite may comprise a calcium phosphate lattice into which, optionally, one or more of Silicon (Si), Fluorine (F), Sulphur (S), Boron (B), Strontium (Sr), Magnesium (Mg), Silver (Ag), Barium (Ba), Zinc (Zn), Sodium (Na), Potassium (K), Aluminium (Al), Titanium (Ti) and Copper (Cu) have been introduced.

Said apatite is preferably a hydroxyapatite. Said apatite is preferably hydroxyapatite. Suitably, 90 to 100 wt %, preferably 95 to 100 wt %, preferably 98 to 100 wt % of said apatite is made up of calcium, phosphorous, oxygen and hydrogen moieties. Said apatite is preferably a hydroxyapatite which consists essentially of calcium, phosphorous, oxygen and hydrogen moieties.

The D50 of said apatite, assessed using laser diffraction and based on a volume distribution, is suitably less than 200 μm, preferably less than 100 μm, more preferably less than 50 μm, especially less than 20 μm. The D50 may be at least 0.1 μm, preferably at least 0.5 μm, more preferably at least 1.0 μm.

Said implant is preferably screw-threaded. It is preferably arranged to be secured in a patient's mandible or maxilla. Said implant is preferably arranged to cooperate with a superstructure. Said implant may include a female or male element which is arranged to cooperate with a male or female element associated with said superstructure. Said implant preferably includes a female element, for example a screw-threaded bore, which is suitably arranged to cooperate with a male element associated with said superstructure. For example, said male element may comprise a screw. Said superstructure may be arranged to be secured to said implant by use of a screw.

A said male or female element associated with said screw preferably includes less than 5 wt %, preferably less than 1 wt %, of hydroxyapatite, more preferably zero wt % hydroxyapatite. A said male or female element associated with said screw preferably includes substantially no apatite of any description.

Said superstructure preferably includes less than 5 wt %, preferably less than 1 wt % of hydroxyapatite, more preferably zero wt % hydroxyapatite. Said superstructure preferably includes substantially no apatite of any description.

Said implant is suitably part of a prosthodontics device which also includes said superstructure, wherein said implant includes hydroxyapatite as described and preferably no part of said prosthodontics device except said implant includes hydroxyapatite as described and preferably no part of said prosthodontics device except said implant includes hydroxyapatite.

Said superstructure preferably comprises a polymeric material which independently comprises a repeat unit of formula I

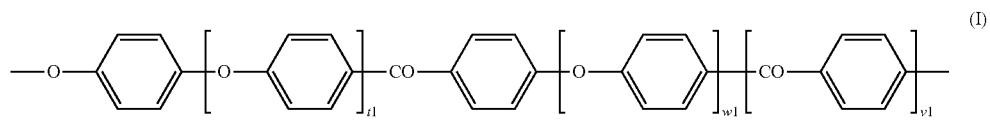

wherein t1 and w1 independently represent 0 or 1 and v1 represents 0, 1 or 2.

Said polymeric material of formula I included in said implant and said polymeric material included in said superstructure are preferably the same. Both preferably comprise a polymeric material of formula I where t1=1, v1=0 and w1=0.

Said superstructure may include an abutment and a framework securable to the abutment. Said abutment preferably comprises a polymeric material of formula I (especially where t1=1, v1=0 and w1=0) and preferably include no hydroxyapatite and preferably no apatite of any description.

Said superstructure preferably includes prosthetic teeth and gums.

Said framework preferably includes an area of thickness less than 2 mm. Said framework preferably includes an area of at least 0.5 cm², preferably at least 1 cm² which has a thickness of less than 2 mm.

Said framework preferably includes an area of thickness less than 1.5 mm. Said framework preferably includes an area of at least 0.2 cm², preferably at least 1 cm² which has a thickness of less than 1.5 mm. Said framework preferably includes an area of less than 1.0 mm. Said framework preferably includes an area of at least 0.5 cm², preferably at least 1 cm² which has a thickness of less than 1.0 mm.

Preferably, the framework includes openings, for example holes which extend through the framework. The holes preferably have an area of less than 10 mm², or less than 8 mm² or less than 6 mm². The holes may have an area of at least 1 mm². The framework suitably includes at least 4, preferably at least 6, more preferably at least 8 holes. Preferably, holes are positioned in regions of said framework which are to be covered with prosthetic teeth and/or gum-like material, suitably to facilitate keying of the prosthetic teeth and/or gum-like material on the framework.

A prosthodontics device which includes said implant and said superstructure may (except for any screw used) include less than 2 wt % of metal, preferably less than 1 wt % of metal, more preferably less than 0.5 wt % of metal, especially less than 0.1 wt % of metal. Said device is preferably substantially metal-free.

According to a second aspect of the invention, there is provided a method of making a dental implant according to said first aspect, the method comprising:

(i) selecting a composition which comprises a polymeric material and an apatite, for example an hydroxyl-containing apatite (especially hydroxyapatite), wherein said polymeric material comprises a polymeric material which comprises a repeat unit of formula (I)

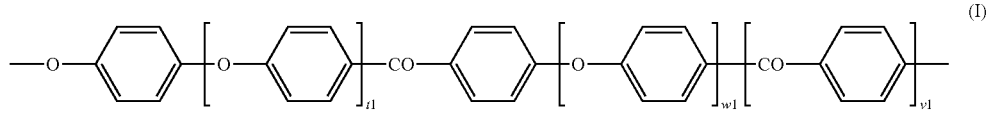

where t1 and w1 independently represent 0 or 1 and v1 represents 0, 1 or 2;

wherein the ratio of the wt % of said polymeric material divided by the wt % of said hydroxyapatite is in the range 1 to 9; and (ii) forming said composition into a shape which defines said dental implant.

Said forming step may comprise machining or moulding, for example injection moulding.

Said implant of the second aspect may have any feature of the implant of the first aspect.

The method may include conditioning the dental implant. Said method may comprise subjecting the implant to a humid atmosphere (e.g. having greater than 20%, 30% or especially greater than 45%, humidity) for at least 5 days, preferably at least 10 days or at least 30 days (and suitably less than 50 days) before use. Said conditioning may be carried out at a temperature in the range 15-100° C., preferably 18-80° C., more preferably 18-50° C. Such conditioning is found to improve mechanical properties of the implant.

According to a third aspect, there is provided a kit comprising a dental implant of the first aspect and a superstructure of the first aspect, wherein said superstructure is suitably arranged to be releasably secured to the dental implant.

According to a fourth aspect, there is provided a method of osseointegrating a dental implant into the mandible or maxilla of a patient, the method comprising:
(i) selecting a dental implant according to the first aspect and/or as made according to the second aspect;
(ii) introducing, for example screwing, said dental implant into the mandible or maxilla;
(iii) leaving the dental implant to osseointegrate, for example over a period of at least 1 week or 1 month.

The invention extends to a dental implant for osseointegration into the mandible or maxilla of a patient, said dental implant being as described according to the first aspect and/or being as made according to the second aspect.

In a fifth aspect, there is provided a prosthodontics device comprising:
(i) an implant part arranged to be osseointegrated into a patient's jaw bone, wherein said implant part comprises a first polymeric material which comprises a repeat unit of formula (I):

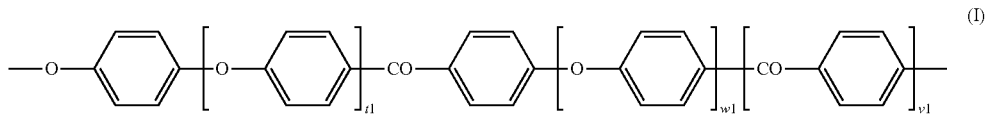

where t1 and w1 independently represent 0 or 1 and v1 represents 0, 1 or 2;
(ii) a crown part secured relative to or arranged to be secured relative to the implant part, wherein said crown part comprises a second polymeric material which comprises a repeat unit of formula (I):

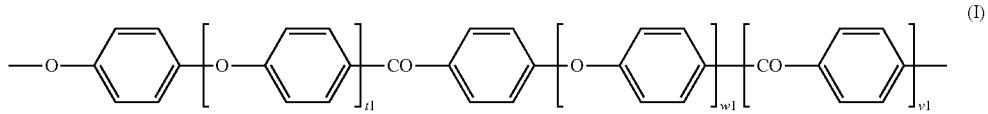

where t1 and w1 independently represent 0 or 1 and v1 represents 0, 1 or 2.

Said first polymeric material may have any feature of said polymeric material of the first aspect. Preferably, said first polymeric material comprises (especially consists essentially of) said repeat unit of formula I wherein t1=1, v1=0 and w1=0.

Said second polymeric material may have any feature of the first polymeric material described. Preferably, said first and second polymeric materials are the same. Preferably, they both comprise (preferably consist essentially of) the same repeat unit of formula I, wherein preferably t1=1, w1=0 and v1=0. Said first and second polymeric materials are preferably polyetheretherketone.

Said implant part may comprise (preferably consist essentially of) a first composition which comprises said first polymeric material. Said first composition preferably includes at least 60 wt %, more preferably at least 70 wt %, of said first polymeric material In a first embodiment, said first composition includes at least 90 wt %, at least 95 wt % or at least 99 wt % of said first polymeric material (especially polyetheretherketone). In a second embodiment, said first composition includes said first polymeric material and an apatite, for example an hydroxyl-containing apatite (especially hydroxyapatite). The inclusion of said apatite may improve osseointegration of the implant part into the mandible or maxilla of a patient in use.

Said implant part is preferably screw-threaded.

In said second embodiment, the ratio of the wt % of said first polymeric material divided by the wt % of said apatite (e.g. hydroxyapatite) is preferably in the range 1 to 9. Unpredictably, it has been found that a dental implant as described has both excellent mechanical properties (which enable implants having thin walls and/or small dimensions to be manufactured) and excellent osseointegration properties.

The ratio of the wt % of said first polymeric material divided by the wt % of said apatite may be in the range 2.3 to 9, is suitably in the range 2.7 to 5.6, preferably in the range 3 to 5, more preferably in the range 3.5 to 4.5, especially in the range 3.8 to 4.2 or 3.9 to 4.1.

Said first composition suitably includes at least 65 wt %, preferably at least 70 wt %, more preferably at least 75 wt % of said first polymeric material, and may include at least 10 wt %, preferably at least 15 wt %, more preferably at least 18 wt % of said apatite. The balance in said first composition may be made up of other fillers, for example colourants. Preferably, in said first composition, the sum of the wt % of said first polymeric material and said apatite is in the range 90 to 100 wt %, more preferably in the range 95 to 100 wt %, especially 99 to 100 wt %.

Said apatite in said first composition of said second embodiment may be as described for the apatite of the first aspect.

Said crown part of the device of the fifth aspect may comprise (preferably consist essentially of) a second composition which comprises said second polymeric material. Said second composition preferably includes at least 90 wt %, preferably at least 94 wt % of said second polymeric material. The balance may include fillers, for example colourants. Said crown part suitably includes less than 5 wt %, preferably less than 1 wt % of hydroxyapatite, more preferably zero wt % hydroxyapatite.

In said prosthodontics device, a coating may be provided on said crown part. The coating may be tooth and/or gum coloured and may be provided to improve aesthetics of the prosthodontics device. The coating may not include a polymeric material of formula I.

Preferably, said prosthodontics device includes an intermediate part secured between or arranged to be secured between the implant part and crown part.

Said intermediate part preferably comprises a third polymeric material which comprises a repeat unit of formula I wherein t1, w1 and v1 are as described above.

Said third polymeric material may have any feature of the first polymeric material described.

Preferably, said first and third polymeric materials are the same. Preferably, they both comprise (preferably consist essentially of) the same repeat unit of formula I, wherein preferably t1=1, w1=0 and v1=0. Said first and third polymeric materials are preferably polyetheretherketone.

Said intermediate part may comprise (preferably consist essentially of) a third composition which comprises said third polymeric material. Said third composition preferably includes at least 90 wt %, preferably at least 94 wt % of said third polymeric material. The balance may include fillers, for example colourants. Said intermediate part suitably includes less than 5 wt %, preferably less than 1 wt % of hydroxyapatite, more preferably zero wt % hydroxyapatite.

As assembled prosthodontics device suitably comprises said implant part secured to said intermediate part; and said intermediate part is secured to the crown part. In said assembly, preferably an imaginary line extending from a point on said implant part via said intermediate part to a point on said crown part includes a polymeric material of formula I as described above (and suitably having any feature of said first polymeric material described) along its entire extent. That is there is preferably no part of the line which does not include at least some of said polymeric material of formula I. Preferably, the entire extent of said line includes at least some polyetheretherketone as described herein. Said line may extend from one outer extremity of said implant part via said intermediate part to said crown part, suitably to an outer extremity of said crown part provided however that a coating which may not comprise polyetheretherketone may be provided on said crown part.

Said assembled prosthodontics device suitably includes at least 70 wt %, preferably at least 75 wt %, more preferably at least 80 wt %, especially at least 85 wt % of a first polymeric material as described, which is, especially, polyetheretherketone. In some embodiment, said device may include greater than 90 wt % or greater than 95 wt % of said first polymeric material, especially polyetheretherketone.

In a first example of said prosthodontics device, said implant part, said intermediate part and said crown part are suitably provided in one piece, wherein said implant part, intermediate part and crown part define a unitary device and/or wherein said parts are permanently secured together. The combination of implant part, intermediate part and crown part is suitably made in one piece, for example by machining.

In a second example of said prosthodontics device, said device may comprise a said implant part which is arranged to be secured to a said intermediate part; and said crown part is also arranged to be secured to said intermediate part. Thus, said device suitably includes three separate parts arranged to be secured together. For example, the implant part may be screw-threaded and arranged to be secured into the maxilla or mandible; said implant part may be arranged to be engaged by a screw associated with said intermediate part to secure the intermediate part to the implant part; and the crown part may be arranged to be secured to the intermediate part, for example by engagement of a screw in a bore.

In a third example of said prosthodontics device, said implant part and said intermediate part are suitably provided in one piece, wherein said implant part and intermediate part define a unitary component and/or wherein said parts are permanently secured together. The combination of implant part and intermediate part is suitably made in one piece, for example by machining.

In a fourth example of said prosthodontics device, said crown part and said intermediate part are suitably provided in one piece, wherein said crown part and intermediate part define a unitary component and/or wherein said parts are permanently secured together. The combination of crown part and intermediate part is suitably made in one piece, for example by machining.

According to a sixth aspect of the invention, there is provided a method of making a prosthodontics device of the fifth aspect which includes the steps of:

(i) selecting a blank from which the implant part and/or crown part can be machined, wherein said blank comprises a polymeric material which comprises a repeat unit of formula (I)

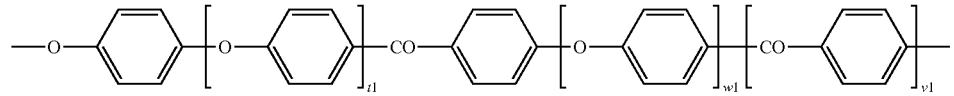

where t1 and w1 independently represent 0 or 1 and v1 represents 0, 1 or 2;
(ii) using digital technology to collate data to define the shape and dimensions of the implant part and/or crown part; and;
(i) machining the blank in dependence upon the data.

The implant part and crown part may be machined from the same blank.

The prosthodontics device of the sixth aspect may have any feature of the prosthodontics device of the fifth aspect. When the prosthodontics device includes an intermediate part as described, said part may be machined from a blank. Preferably, the implant part, crown part and intermediate part are machined from the same blank.

In step (ii), digital technology is used to collate data on the region into which the prosthodontics device is to fit. Step (ii) preferably includes scanning a region into which the prosthetic device is to fit (e.g. scanning a patient's mouth) or scanning of a model of a region into which the device is to fit. Preferably, data is collated from a model, for example a cast, obtained of a patient's mouth and/or dentition. Step (ii) may comprise use of Computer-aided design (CAD) technology.

The method preferably includes a step prior to step (ii) of taking an impression of a patient's mouth. The impression may be used to collate said data. The method preferably involves a CAD/CAM technique whereby data is collated as aforesaid and computer-aided manufacture (CAM) is undertaken in step (iii). Thus, in step (iii), a computer suitably controls the machining of the blank.

Preferably, the selected blank is positioned in a CAD/CAM machine and the machine is arranged to machine the blank in dependence upon the data.

Preferably, machining of said blank is undertaken using at least 5-axis machining, suitably under computer control. In some cases, higher axis (e.g. 7-axis) machining may be undertaken. Machining in step (iii) suitably comprises milling. The work piece is suitably cooled during machining so as to control crystallinity of the machined blank.

Any invention described herein may be combined with any feature of any other invention or embodiment described herein mutatis mutandis.

Specific embodiments of the invention will now be described, by way of example, with reference to the following figures, in which.

Figures 7A, 7B:
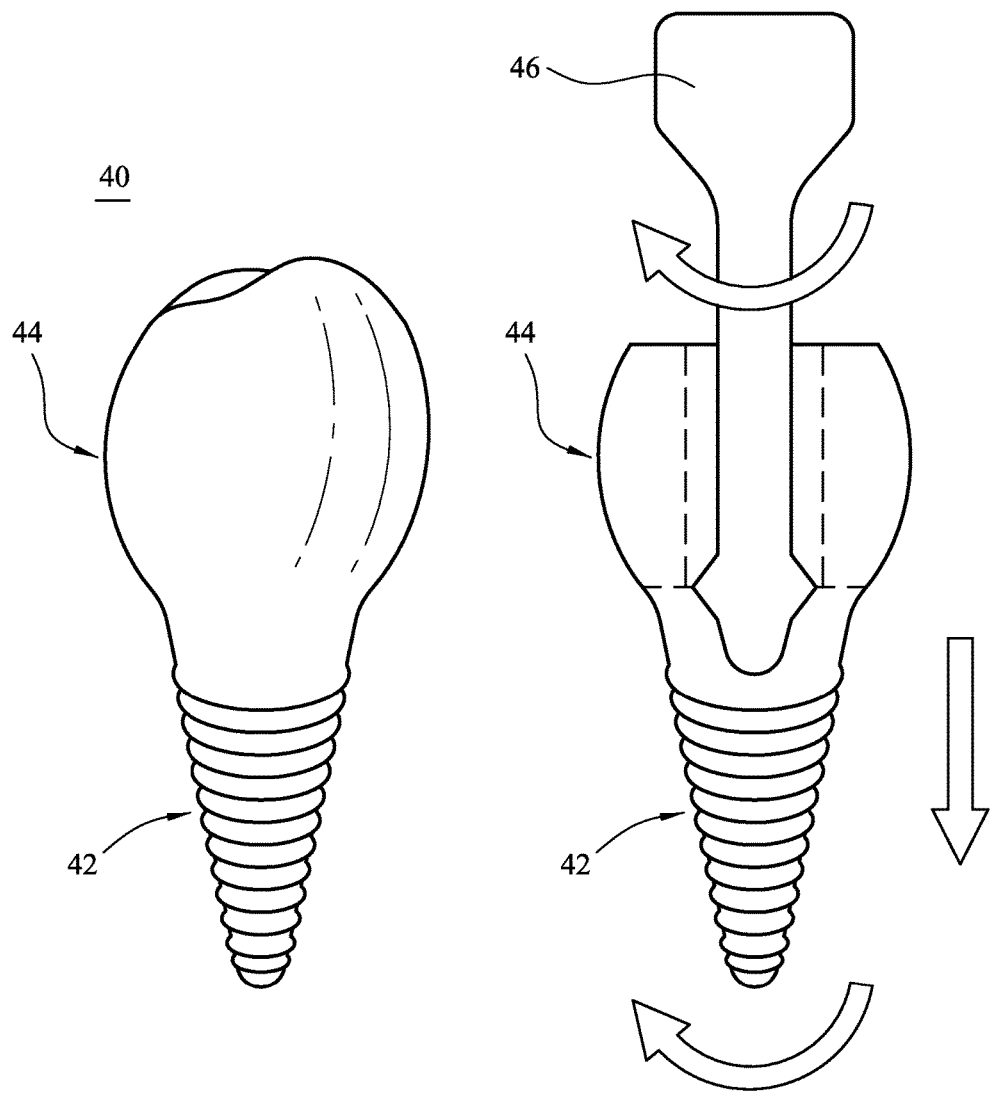

FIG. 7*a* is a view of a one-piece prosthodontics device; and

FIG. 7*b* is a partially cut-away view illustrating how the device of FIG. 7*a* may be screwed into a patient's jawbone.

The following materials are referred to hereinafter:

Hydroxyapatite (HA) obtained from Plasma Biotal Ltd. It has a $D_{50}$ measured by laser diffraction of 5.18 µm, a surface area of 5.91 m$^2$/g and a bulk density of 0.62 g/ml$^3$.

PEEK OPTIMA LTI—polyetheretherketone obtained from Invibio Ltd.

In the figures, the same or similar parts are annotated with the same reference numerals.

In the following examples, Example 1 describes the manufacture of composite material comprising polyetheretherketone (PEEK) and hydroxyapatite (HA); Example 2 provides a general procedure for making injection moulded components; Examples 3 to 6 describe preparation of composite materials comprising different levels of PEEK/HA; Example 7 describes bioactivity testing of PEEK/HA material; Example 8 provides results of pre-clinical studies; and Example 9 provides a method for improving mechanical properties of a PEEK/HA component. Thereafter, further embodiments are described with reference to FIGS. 3 to 8.

EXAMPLE 1—MANUFACTURE OF COMPOSITION COMPRISING POLYETHERETHERKETONE (PEEK) AND HYDROXYAPATITE (HA)

Polyetheretherketone (PEEK) obtained in the form of PEEK-OPTIMA® LTI (Invibio Biomaterial Solutions, UK) having a melt viscosity (MV) of 0.44 KNsm$^{-2}$ was dried to remove water (it absorbs water during storage). The PEEK was in the form of granules of approximately 3 mm by 2 mm size. Hydroxyapatite (HA) in the form of particles having mean particle size of about 5 µm was selected.

The PEEK and HA were mixed in a twin screw compounder (extruder) which heated the mixture to between 360° C. and 400° C. (with a temperature of 400° C. at the extruder output) to melt the PEEK. The PEEK was introduced to the extruder at a point upstream from the introduction of HA to the extruder. The PEEK was heated and conveyed through the extruder such that the PEEK was in a molten state within the extruder before the HA was added. The mixture of HA and molten PEEK was then conveyed further through the extruder to mix the PEEK and HA. A PEEK and HA composite was extruded from the extruder and pelletized.

The PEEK and HA were added to the extruder in a ratio such that the output of the extruder was a PEEK and HA composite which comprised 10 wt % of HA.

The extruder comprised a normal screw profile fabricated from stainless steel with a minimum L/D ratio of 45:1. At the extrusion end a twin hole die with a 4 mm orifice and pelletizer was used. The main screw rotation speed was set at 150-250 rpm. The screws were intermeshing counter-rotating screws having a length of around 1 m and a diameter of around 40 mm. Laces of approximately 2 mm diameter were chopped to lengths of approximately 3 mm to define the PEEK and HA composite pellets.

EXAMPLE 2—GENERAL PROCEDURE FOR MAKING INJECTION MOULDED COMPONENTS

Pellets (e.g. those of Example 1) were injection moulded to produce a bioactive component. An injection moulding machine used comprised a heated barrel through which the pellets were conveyed by a screw. The barrel was heated to temperatures of between 360° C. and 375° C. such that the polymeric material within the pellets melted as they were conveyed through the barrel such that a melt was produced. The melt was then injected through a nozzle into a mould with the mould tool being heated to between 200° C. and 220° C.

Mechanical properties, including Izod impact strength (Notched) (ISO 180), flexural strength (ISO 178), flexural modulus (ISO 178), tensile strength (ISO 527), and strain at break (ISO 527) of a test specimen were determined and the results are shown in Table 1.

EXAMPLES 3 TO 6

The method of Example 1 was repeated but the ratio of PEEK to HA was adapted such that the output of the extruder was a PEEK and HA composite which comprised a different wt % of HA, as detailed in Table 1.

TABLE 1

| Example No. | PEEK (wt %) | HA (wt %) |
|---|---|---|
| 3 | 80 | 20 |
| 4 | 70 | 30 |
| 5 | 60 | 40 |
| 6 | 50 | 50 |

The PEEK and HA composite pellets produced were injection moulded as described in Example 2 to produce bioactive components. Mechanical properties of components made were determined and the results are shown in Table 2.

COMPARATIVE EXAMPLE 1

Polyetheretherketone (PEEK) obtained in the form of PEEK-OPTIMA® (Invibio Biomaterial Solutions, UK) was used in an injection moulding machine and injection moulded to produce a component following the general procedure of Example 2. Mechanical properties were determined for comparison with the components of Examples 1 and 3 to 6 and the results are shown in Table 2.

Results

The results of the mechanical tests are detailed in Table 2 below:

TABLE 2

| Property | Comparative Example (No HA) | Example 1 (10% HA) | Example 3 (20% HA) | Example 4 (30% HA) | Example 5 (40% HA) | Example 6 (50% HA) |
|---|---|---|---|---|---|---|
| Impact Strength (KJ/m2) | 7.33 | 7.4 | 6.1 | 5.2 | 4.6 | 4.6 |
| Flexural strength (MPa) | 162.45 | 156.1 | 156.0 | 154.2 | 139.2 | 118.8 |
| Flexural modulus (GPa) | 3.96 | 4.33 | 4.72 | 5.61 | 6.67 | 8.02 |
| Tensile Strength (MPa) | 99.25 | 88.7 | 88.7 | 81.8 | 73.5 | 75.5 |
| Strain at Break (%) | 35.8 | 24.09 | 8.8 | 3.98 | 2.24 | 1.27 |

It was found that PEEK could be successfully compounded with HA up to 50 wt % HA, without significant difficulties and with no reaction observed between the two components. The mean mechanical values for impact strength, flexural strength, flexural modulus, tensile strength, and strain at break were plotted (plots not shown) against the filler content and compared with those of the unfilled PEEK to determine optimum HA levels. From this it was concluded that 20 wt % of HA (Example 3) gave the optimum level to allow HA to be present at sufficient levels to provide desirable bioactivity to the component without significant detriment to the physical properties

EXAMPLE 7—BIOACTIVITY TESTS

PEEK containing 20% by weight HA (Example 3) was chosen for further bioactivity studies due to the limited effects on material mechanical properties compared to PEEK alone (Comparative Example 1).

Bioactivity of the PEEK/HA was determined by the ability to form apatite on the surface of the material in a simulated body fluid (SBF) using SBF-JL2 as prepared and described in Bohner and Lemaitre (Bohner M, Lemaitre J./Biomaterials 30 (2009) 2175-2179) and compared with controls comprising PEEK alone.

The SBF-JL2 was produced using a dual-solution preparation (Sol. A and Sol. B) having the following composition for 2 liters of final fluid:

| Starting Materials Formula | MW [g/mol] | Purity [–] | Sol. A | Sol. B |
|---|---|---|---|---|
| | | | Weights of starting materials [g/L] | |
| NaCl | 58.44 | 99.5% | 6.129 | 6.129 |
| NaHCO$_3$ | 84.01 | 99.5% | 5.890 | |
| Na$_2$HPO$_4$ · 2H$_2$O | 177.99 | 99.0% | 0.498 | |
| CaCl$_2$ | 110.99 | 95.0% | | 0.540 |
| | | | Volume of HCl solution (mL/L) | |
| HCl 1.00M | Aq. Sol. | [mL/L] | 0.934 | 0.934 |

Use of this in vitro method of examining apatite formation as a means of predicting in vivo bone bioactivity is both widely used and accepted (Kokubo T, Takadama H. How useful is SBF in predicting in vivo bone bioactivity? Biomaterials 2006; 27(15):2907-2915). Samples were immersed in SBF for 1, 3 and 7 days on a rotating platform at 37° C. with 5% $CO_2$ and 100% humidity. X-ray photoelectron spectroscopy (XPS), scanning electron microscopy (SEM), and attenuated total reflectance Fourier transform infrared spectroscopy (ATR-FTIR) were used to analyze the bioactive elements present on the surface of the specimens following immersion in SBF.

SEM analysis of the surface of PEEK controls and PEEK/20% HA composite revealed the formation of spherical crystals on the surface after immersion in SBF. These were more numerous and apparent on the PEEK/20% HA samples and these were observed as early as 1 day post-immersion in SBF, suggesting increased apatite formation.

Detailed Ca2p and P2p XPS spectra revealed that although Ca and P were identified on the surface of both materials, only elemental ratios present on the PEEK/20% HA samples were conducive to bone formation with a Ca/P ratio of 1.66, close to the theoretical value for hydroxyapatite. Meanwhile, the ratios of the depositions on the control PEEK were more variable (>1.67), and indicative of non-hydroxyapatite calcium phosphate formations.

Following immersion in SBF for 1 day, ATR-FTIR surface analysis was performed on PEEK/20% HA and control PEEK samples to semi-quantify the degree of apatite deposition and detect functional groups. A significant peak was observed at 1015 cm$^{-1}$, most likely arising from the structural P—O bond of phosphate groups. The ratio of absorption at 1015 cm$^{-1}$ to 1645 cm$^{-1}$ (characteristic of PEEK) was measured and showed an increased ratio on PEEK/20% HA samples compared with control PEEK, confirming the XPS findings indicating greater apatite formation on the PEEK/20% HA samples.

Surprisingly it has been found that despite the low proportion of HA in the component (only 20% by weight) sufficient HA is available at the surface of the component to impart bioactive properties to the component and promote apatite formation.

EXAMPLE 8—ASSESSMENT OF DEGREE OF DIRECT IMPLANT-BONE CONTACT IN AN OVINE PRE-CLINICAL STUDY

Cylindrical dowels of the composition of Example 3 and PEEK-OPTIMA were implanted in an established ovine model. Implants were placed in sheep tibia cortical bone for 4 weeks and 12 weeks. At the end of each time point, implants and surrounding bone were harvested and embedded in PMMA. Tissue sections were stained for histology using methylene blue and basic fuchsin. Histology images were graded on a semi-quantitative scale by two blinded observers to determine the percent bone ongrowth. At both the 4 week and 12 week time points, the percentage of direct bone contact was higher with the composition of Example 3 compared with PEEK-OPTIMA alone.

Figure 1:
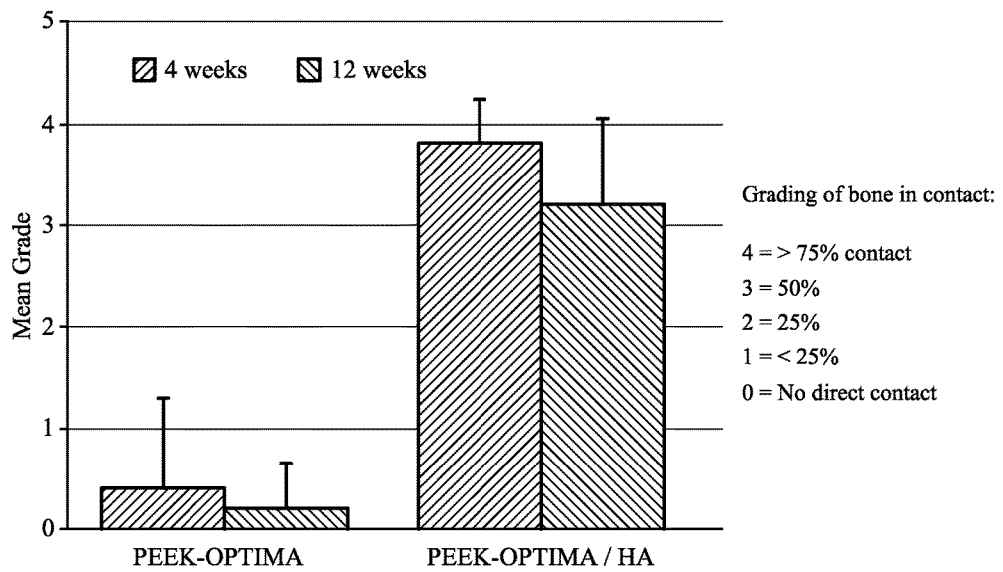
FIG. 1 is a graph showing the results of grading of bone.
Figure 2:
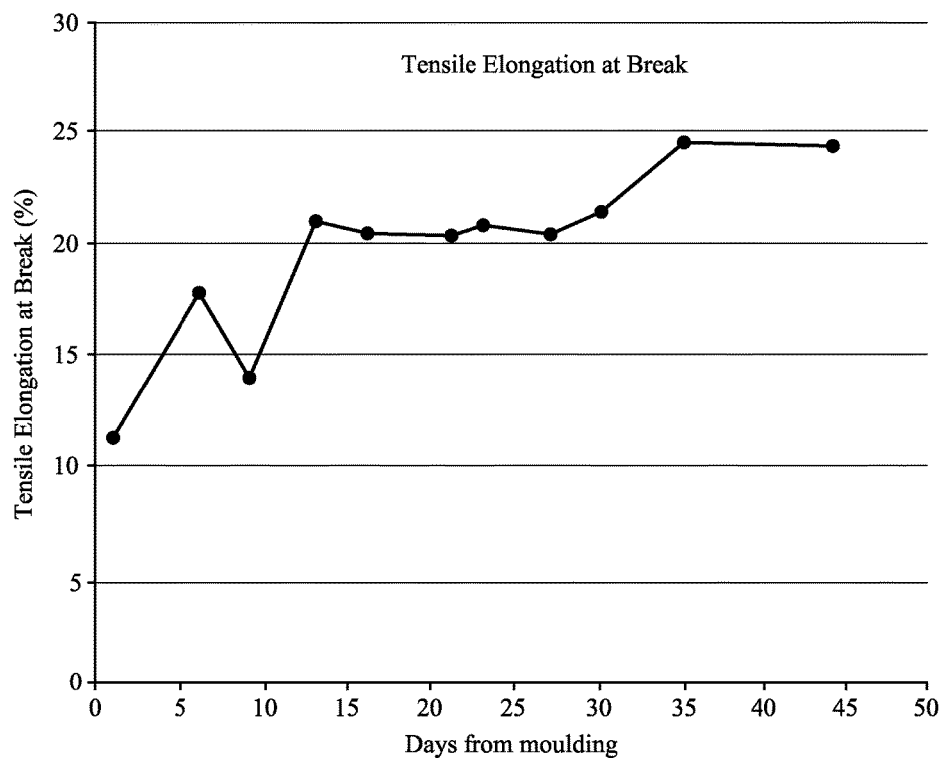
FIG. 2 is a graph of Tensile Elongation v. Days from moulding for conditioned components.

Results are provided in FIG. 1 which shows the grading of bone in contact for components made from Comparative Example 1 and Example 3 materials.

Granules comprising the material of Example 3 may advantageously be used to produce prosthodontics devices, for example implants, using a range of methods, for example:
  (i) Milling of discs made from the material of Example 3 using CAD-CAM technology as described in WO2013/070493.
  (ii) Injection moulding
  (iii) Compression moulding.
  (iv) Use of dental press system (casting).

It has been found that components made from a composition comprising PEEK and HA can be conditioned yielding components of improved mechanical properties. This is discussed in the following example.

EXAMPLE 9

Injection moulded sample components comprising PEEK (80 wt %) and HA (20 wt %) were conditioned at 23° C. and 50% humidity for a length of time as indicated in FIG. 1. At each time point, tensile elongation at break of five samples. Measurements of tensile elongation at break were conducted in accordance to ISO527. A substantial increase in tensile elongation at break was observed for the conditioned samples when compared with the initial moulded samples.

The embodiments described hereinafter address the second object of preferred embodiments of the invention, with reference to FIGS. 3 to 8.

Figure 3:
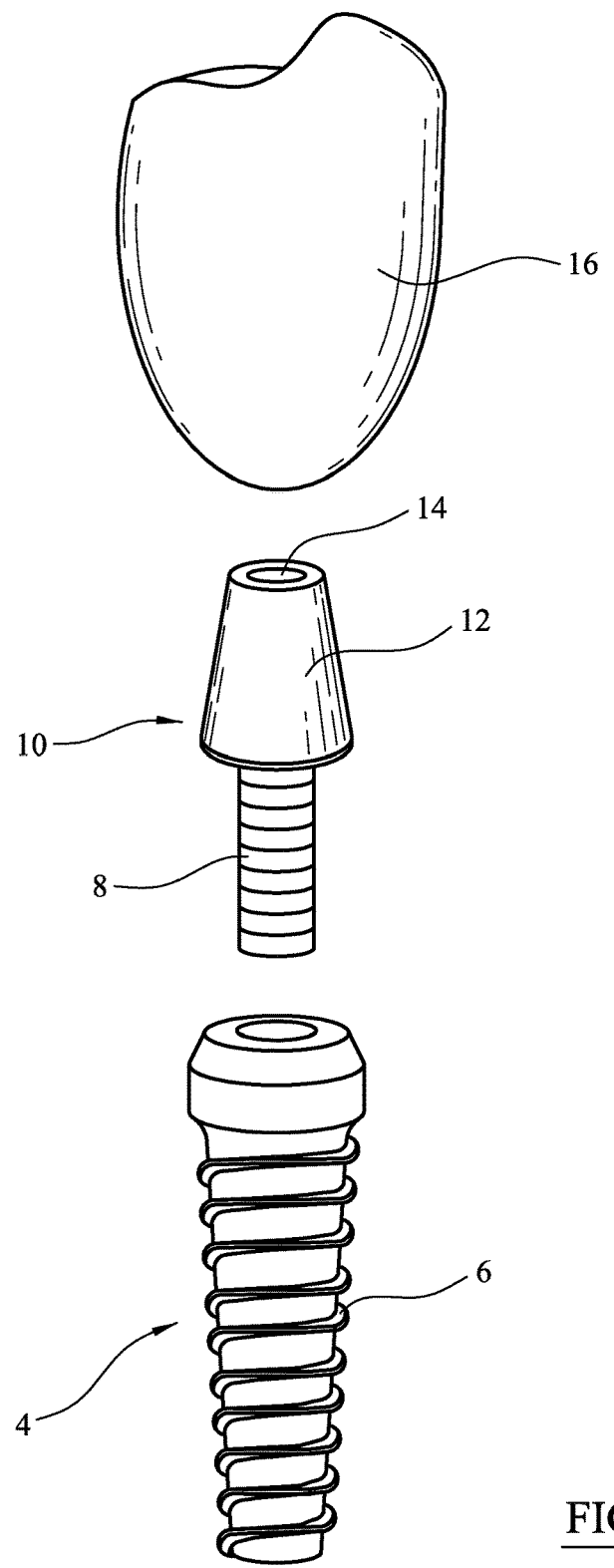
FIG. 3 is an exploded view of a prosthodontics device.
Figures 4, 5, 6:
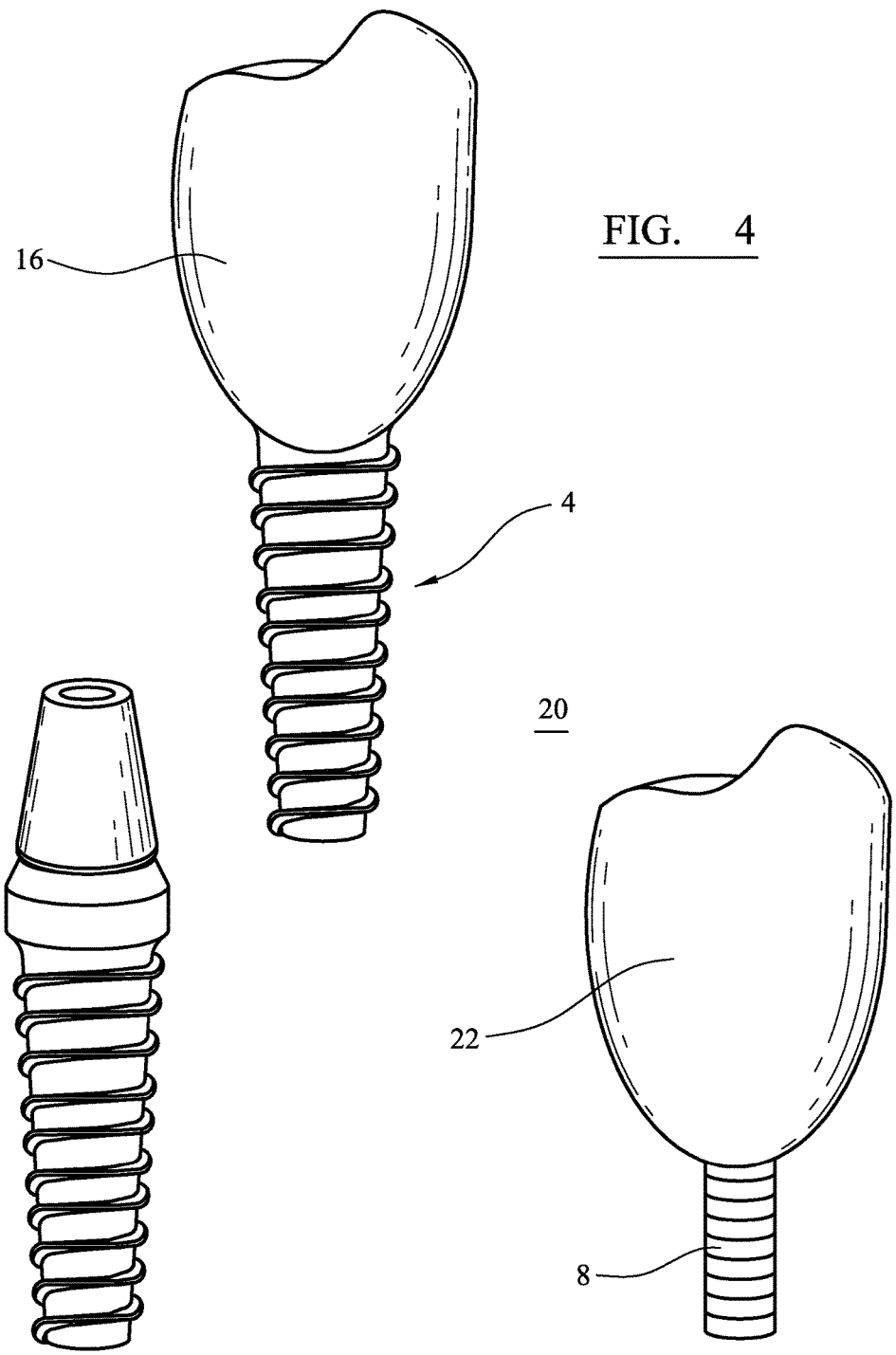
FIG. 4 is an assembled view of the device of FIG. 3.
FIG. 5 is a view of a one-piece implant/abutment component.
FIG. 6 is a view of a combined, one-piece crown/abutment component.

In a first embodiment, a prosthodontics device 2, shown in FIG. 3, comprises a dental implant 4 which includes an outer screw-threaded region 6 which enables the implant to be threaded into a bore (not shown) which is drilled in a patient's mandible or maxilla. The implant 4 includes an internal screw-threaded region (not shown) which is arranged to screw-threadedly engage screw-threaded region 8 of an abutment 10. Abutment 10 includes a head 12 which includes a bore 14 which includes an internal screw-threaded region (not shown). A crown 16 is arranged to be secured to the abutment 12 by engagement of a screw (not shown) in a bore (not shown) defined in the prosthetic tooth, the screw extending and being secured in the internal screw-threaded region of the abutment. The assembled structure is shown in FIG. 4.

The dental implant 4 may be made from polyetheretherketone (PEEK) (PEEK-OPTIMA LT1 obtained from Invibio Limited). It may be made by injection moulding, by compression moulding or by machining of a rod made from PEEK. It may be a commodity item which need not be customized for a particular patient. It may though be provided in a range of different sizes.

The abutment 10 may also be made from PEEK as described for the implant 4. It also may be a commodity item which need not be customized, at least at the time of manufacture, for a particular patient. It may also be provided in a range of different sizes. Alternatively, in some cases, the abutment may be customized for particular patients and made by a CAD-CAM process The implant and abutment may be assembled as follows:

Firstly, a bore is drilled into the patient's mandible or maxilla and the implant 4 is screwed into the bore. It is then left for several weeks to osseointegrate. A temporary abutment or healing cap might be used during this healing phase of the gum and oseointegration of the implant. In this case, once osseointegrated, the abutment 10 is screw-threadedly secured to the implant so the head 12 of the abutment extends above the patient's mucosa. If an immediate loading approach is taken, the final abutment is screwed into the implant after implant placement and before osseointegration has taken place. Once osseointegrated, the abutment 10 is screw-threadedly secured to the implant so the head 12 of the abutment extends above the patient's mucosa. Subsequently, a dentist may, if appropriate, mill the abutment to adjust it and/or facilitate attachment of the crown. Such milling with the abutment in situ in a patient's mouth is readily possible.

Next, a mould is taken of the appropriate part of the patient's mouth which includes the abutment 10 using a standard impression tray. The mould is then poured with dental plaster and allowed to set. The mould is then scanned to collate relevant CAD data which is input into an 5-axis CAD-CAM machine. The machine then produces the crown 16 from a PEEK disc. Thus, like the implant 4 and abutment 10, the crown 16 is made from PEEK.

Prior to assembly, the crown 16 may be finished by application of dental veneers to define an aesthetically acceptable prosthetic tooth. Thereafter, the crown is secured in position on the abutment. This may be achieved by engagement of a screw with both the crown and abutment (via bore 14) in conjunction, optionally, with cements. Advantageously, since both the crown and abutment are made from PEEK a cement may be selected which is optimised for adhesion to PEEK rather than a compromise cement being selected as would be the case if the crown and abutment were made from different materials.

The arrangement described may have a number of advantages which may include the following:
  (i) Since the implant 4 and abutment 10 are made from a strong flexible material (i.e. PEEK), the combination will be flexible which may provide improved mouth feel;

(ii) The flexibility of the implant and/or abutment 10 may reduce stress shielding (i.e. the implant working loose);

(iii) Wear, for example, fretting wear between the implant and abutment and/or between abutment and crown may be reduced;

(iv) Ease of precision manufacture of the components;

(v) By virtue of (iv) and the nature of the material used, the combination of implant 4, abutment 10 and crown 16 may be cheaper to manufacture, supply and fit to a patient;

(vi) By virtue of the ability to mill the abutment in situ, minor adjustments may be made in situ, reducing time and expense of fitting the prosthodontics device;

(vii) The flexibility of the implant and/or abutment 10 may provide a shock absorbing benefit and preserve the underlining bone;

(viii) Complete metal free solution, which might provide an alternative to patients that are allergic to metal ions and that cannot accept a metal dental implant.

In a second embodiment, a single component may define both the implant and abutment. The component may be as shown in FIG. 5. The component may be produced in a single piece, for example by machining a rod, or by moulding (e.g. injection or compression moulding). Thus, there is no means of releasably securing the implant and abutments parts of the component. The component may be made from PEEK.

In use, the component is screwed into the mandible or maxilla and allowed to osseointegrate. Then the crown is prepared and fitted as described for the first embodiment.

Provision of the component may be feasible due to the precision with which it may be made coupled with the possibility of a dentist being able to mill the abutment in situ. Use of the component may also be advantageous for the reasons referred to under points (i) to (viii) for the first embodiment. Furthermore, as the component may be specific to each patient, it may be adapted to follow a patient's gum line in a more exact manner, with smaller margins. The ability to design the patient gum line into the abutment should allow for an immediate improved aesthetic result.

In a third embodiment, illustrated in FIG. 6, there is provided a combined component 20 which incorporates an abutment part which includes a screw-threaded region 8 for cooperation with an implant which may be as described in FIG. 3. The abutment part is suitably shaped to engage the implant in the same manner as the abutment 10 engages the implant 4 of FIG. 3. The component 20 also includes a crown part 22.

In the third embodiment, an implant is screwed into the mandible or maxilla as described with reference to FIG. 3 and the component 20 may subsequently be engaged with the implant.

The third embodiment may have advantages as described for the other embodiments. In addition, since the prosthodontics device comprises only two components (i.e. implant and component 20), it may be significantly cheaper to manufacture compared to other devices.

In a fourth embodiment, shown in FIGS. 7*a* and 7*b*, a one-piece component 40 includes a threaded implant part 42 and a crown part 44. The component 40 is made in one-piece from PEEK using a CAD-CAM machine as described in the first embodiment. This involves: digitally scanning a patient's mouth and bone situation; planning the implant location and its insertion digitally; design of the component; testing the component in digital articulators (which are based upon the patient's digital scan) and simulate the behaviour of the component 40 in the patient's mouth; and milling to define component 40. As illustrated in FIG. 5*b*, the component includes a bore providing access to and allowing cooperation with a tool 46 by means of which the component can be screwed into the mandible or maxilla. The dimensions of the component 40 are such that it can be rotated to screw it into the mandible or maxilla without being blocked by teeth adjacent to the gap in which the component is to be placed. After insertion, the bore may be closed and the crown part 44 finished by conventional means.

Components as described (e.g. in FIGS. 3 and 5) may be used to secure bridges carrying multiple crowns and/or teeth in position. For example, first and second implants (e.g. both being the same as implant 4 of FIG. 1) may be secured at spaced apart positions within a patient's mouth. Respective abutments 10 may then be secured to the implants 4. A mould may then be taken as described according to the first embodiment and a bridge incorporating crowns, and being arranged to engage the abutments, may be made from PEEK, using a CAD-CAM machine as described in the first embodiment. Thus, both the implant, bridge and crowns are made from PEEK. The bridge may be secured in position by screws which are engaged with the bridge and implants. The assembly may be finished by conventional techniques.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A method of making a dental implant, the method comprising:

(i) selecting a composition which comprises a polymeric material and an apatite, wherein said polymeric material comprises a polymeric material which comprises a repeat unit of formula (I)

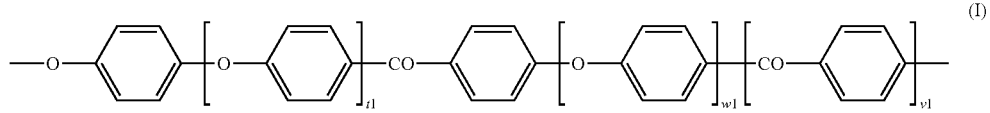

wherein t1 and w1 independently represent 0 or 1 and v1 represents 0, 1 or 2;

wherein the ratio of the wt % of said polymeric material divided by the wt % of said apatite is in the range 1 to 9;

(ii) forming said composition into a shape which defines said dental implant; and (iii) subjecting the implant to a humid atmosphere which comprises greater than 20% humidity for at least five days and a temperature in the range of 15° C. to 100° C. for at least five days.

2. A method according to claim 1, wherein the dental implant is configured to cooperate with a superstructure such that the superstructure is releasably securable to the dental implant.

3. A method according to claim 1 wherein the polymeric material has a repeat unit of formula I, wherein t1=1, v1=0 and w1=0.

4. A method according to claim 1, wherein the polymeric material has a melt viscosity (MV) of at least 0.09 kNsm$^{-2}$ to 0.5 kNsm$^{-2}$.

5. A method according to claim 1, wherein the level of crystallinity of the polymeric material, measured by DSC, is greater than 25%.

6. A method according to claim 1, wherein the ratio of the wt % of the polymeric material divided by the wt % of the apatite is in the range 2.3 to 9.

7. A method according to claim 1, wherein the ratio of the wt % of the polymeric material divided by the wt % of the apatite is in the range 3.8 to 4.2.

8. A method according to claim 1, wherein the composition includes at least 65 wt % of the polymeric material and includes at least 10 wt % of the apatite; and the sum of the wt % of the polymeric material and the apatite is in the range 90 to 100 wt %.

9. A method according to claim 1, wherein the apatite is a hydroxyapatite.

10. A method according to claim 1, wherein said apatite is a hydroxyapatite which consists essentially of calcium, phosphorous, oxygen and hydrogen moieties.

11. A method according to claim 1, wherein the D50 of said apatite, assessed using laser diffraction and based on a volume distribution, is less than 200 μm.

12. A method according to claim 1, wherein the D50 of said apatite, assessed using laser diffraction and based on a volume distribution, is less than 20 μm.

13. A method according to claim 1, wherein the dental implant is arranged to cooperate with a superstructure, wherein said implant includes a female or male element which is arranged to cooperate with a male or female element associated with said superstructure.

\* \* \* \* \*